United States Patent [19]
Parodi

[11] Patent Number: 5,250,070
[45] Date of Patent: Oct. 5, 1993

[54] LESS TRAUMATIC ANGIOPLASTY BALLOON FOR ARTERIAL DILATATION

[76] Inventor: Juan C. Parodi, Blanco Encalada, 1543 Buenos Aires, Argentina

[21] Appl. No.: 705,698
[22] Filed: May 28, 1991
[51] Int. Cl.$^5$ .............................. A61M 29/02
[52] U.S. Cl. .................... 606/194; 604/101; 604/96
[58] Field of Search .......... 600/18; 604/96–103; 606/192–196; 128/207.14, 207.15

[56] References Cited

U.S. PATENT DOCUMENTS

| | | | |
|---|---|---|---|
| 1,115,224 | 10/1914 | McAllum | 604/97 |
| 2,701,559 | 2/1955 | Cooper | 604/103 X |
| 4,018,231 | 4/1977 | Wallace | 604/100 X |
| 4,141,364 | 2/1979 | Schultze | 604/96 |
| 4,471,776 | 9/1984 | Cox | 128/207.15 |
| 4,878,495 | 11/1989 | Grayzel | 604/101 X |
| 4,881,939 | 11/1989 | Newman | 600/31 |
| 4,927,412 | 5/1990 | Menasche | 604/96 |
| 5,002,531 | 3/1991 | Bonzel | 604/96 |
| 5,041,125 | 8/1991 | Montano, Jr. | 606/192 |
| 5,090,958 | 2/1992 | Sahota | 604/98 |

FOREIGN PATENT DOCUMENTS

| | | | |
|---|---|---|---|
| 0344530 | 12/1989 | European Pat. Off. | 604/96 |
| 8101098 | 4/1981 | PCT Int'l Appl. | 604/96 |
| 1327858 | 8/1973 | United Kingdom | 604/96 |

*Primary Examiner*—John D. Yasko
*Assistant Examiner*—Adam J. Cermak
*Attorney, Agent, or Firm*—Christensen, O'Connor, Johnson & Kindness

[57] ABSTRACT

An angioplasty balloon (1) for less traumatic arterial dilation is carried on a part (5) of a catheter (2), the catheter having lumens for inflating the balloon. The surface of the balloon that contacts the endothelium of the vessel being treated is irregularly formed, defining a plurality of grooves and radially projecting parts (7) therebetween.

6 Claims, 3 Drawing Sheets

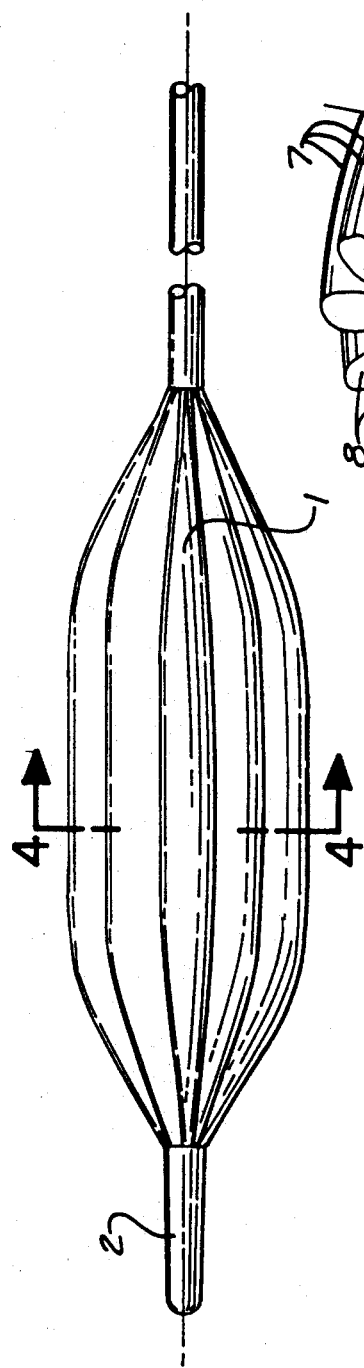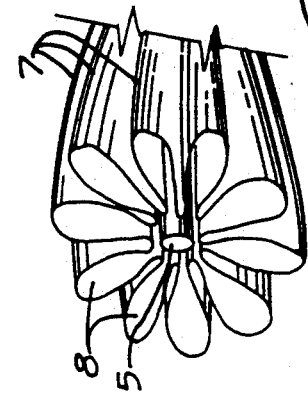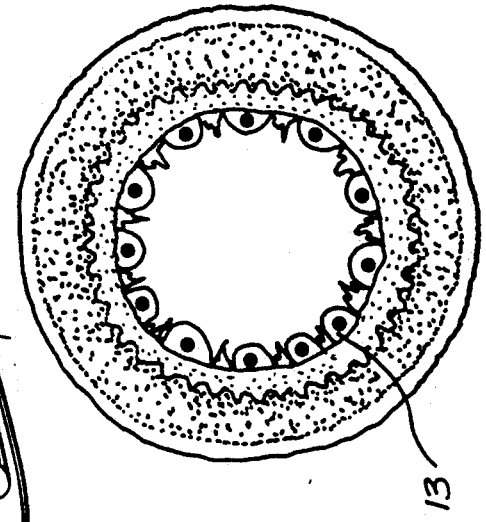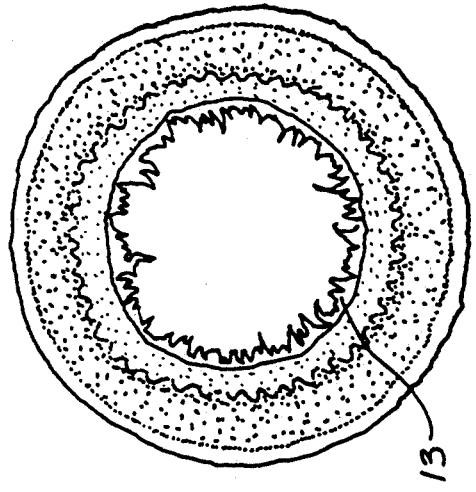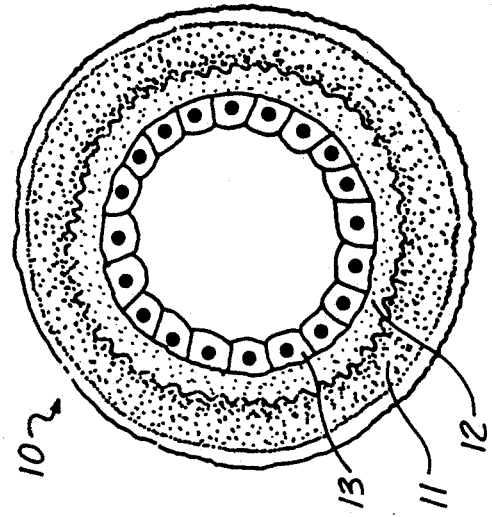
FIG. 3.
FIG. 4.
FIG. 5A.
FIG. 5B.
FIG. 5C.

LESS TRAUMATIC ANGIOPLASTY BALLOON FOR ARTERIAL DILATATION

TECHNICAL FIELD OF THE INVENTION

This invention deals with a less traumatic angioplasty balloon for arterial dilatation and more precisely with a new balloon for dilatation to be used in angioplasty.

The percutaneous transluminal coronary angioplasty by using balloons is a known treatment in the case of arterial stenosis or occlusions since its introduction by Andreas Gruntzig.

Nevertheless the results obtained have not been regularly good in all cases.

At present, specially in the case of treatments of stenosis in the coronary arteries, the technique of using dilatable balloons introduced in the arteries is the more often used.

The above mentioned technique is described in the article "Non operative dilatation of coronary artery stenosis: percutaneous transluminal coronary angioplasty" from A. R. Gruntzig, A. Senning y W. E. Seingenthaler, published in the "New England Journal of Medicine" 301: 61-68, 1979.

In the cited article the type of balloon used nowadays is described, which has a plain surface and therefore the contact thereof with the artery wall is uniform and so the whole endothelium receives the pressure of the balloon wall.

This is the cause of the endothelial damage produced during tansluminal angioplasty, which at the same time generates several events that expedite the production of mio-intimal hyperplasia, that causes the majority of mediate re-stenosis in the treated arteries.

Adhesion of platelets, white blood cells and monocytes is seen specially in the places where there is endothelial denudation.

The two major problems after initially successful arterial balloon angioplasty are acute occlusion and re-stenosis after a variable period of time, usually one to three months.

The endothelial damage is one of the main facts considered responsible, or at least related, to the development of these changes.

The standard balloon used routinely for angioplasty regularly produces endothelial damage represented by denudation of the endothelial layer.

Endothelial denudation and collagen exposure produces the adhesion of platelets, white blood cells and monocytes.

The adhesion of these cells and particles could produce an occlusion of the vessel.

In usual cases, however, acute occlusion does not occur, but, the platelets and blood cells secrete some substances such as the growth factors that promotes changes in the phenotype of the smooth muscular cells of the media.

These activated cells reproduce and migrate to the intima, producing the phenomenom of re-stenosis after a variable period of time, usually one to three months.

Endothelial cells rapidly reproduce and cover the area of denudation.

These new cells, however, are immature cells with abnormal function.

This cell dysfunction lasts weeks or months and in occasions never achieve again normal function.

That means that even with endothelium covering the intima of the artery, intima hyperplasia could ensue.

Another consequence of endothelial dysfunction is the lack of production and/or release of the endothelial derived relaxing factor (EDRF), causing motor dysfunction and a diminished antithrombogenic activity.

In consequence, present technique of dilatation via balloon produces a trauma due to the whole endothelium receiving the pressure causing the subsequent damage, which is avoided with this invention.

With reference to this invention, it is usual finding in arteries with artherosclerosis that the lesion is not always homogeneous, not only on the surface but in the entire wall of the artery, for example, the plaque could be occupying only half of the artery, sparing the rest.

SUMMARY OF THE INVENTION

The advantage of the device of this invention is that not all the endothelium receives the pressure of the balloon avoiding an endothelial extensive damage caused by the angioplastic balloon.

Another advantage of the invention is that the angioplastic balloon can be adapted to the specific characteristics of a given artery.

The main object of the invention is a less traumatic angioplasty balloon for arterial dilatation of the type inflatable by means of respective lumens existing in the catheter used for the introduction of the balloon, characterized in that the surface of the balloon that contacts the endothelium of the vessel being treated has an irregular surface showing grooves and projecting parts.

In a preferred embodiment of the invention the irregular surface are longitudinal grooves.

In said preferred embodiment of the invention said grooves are placed in angle with the axis and when intercrossing they form a net shape.

In another preferred embodiment of the invention said irregular surface are projections orderly placed along the surface.

In still another embodiment of the invention the irregular surface of the balloon is formed by an engraved sheet stuck to the balloon inner wall.

In another embodiment of the invention the grooved surface of the balloon is defined by the fact that the balloon is divided into a group of cylindrical balloons arranged in parallel with a common entrance.

BRIEF DESCRIPTION OF DRAWINGS

The main object and the advantages of the device will be noticed in the following description of a preferred embodiment of the invention, with references to the enclosed drawings, in which:

FIG. 3 is a side view of another preferred embodiment of the invention;

FIG. 4 is a perspective view of the cross section of the balloon pointed out in FIG. 3;

FIGS. 5a, 5b and 5c are views of a cross section of a vessel showing a normal vessel, a vessel treated with the known balloon and the effect obtained in the vessel when treated with the balloon of the invention.

DETAILED DESCRIPTION OF THE PREFERRED EMBODIMENTS

Figure 1:
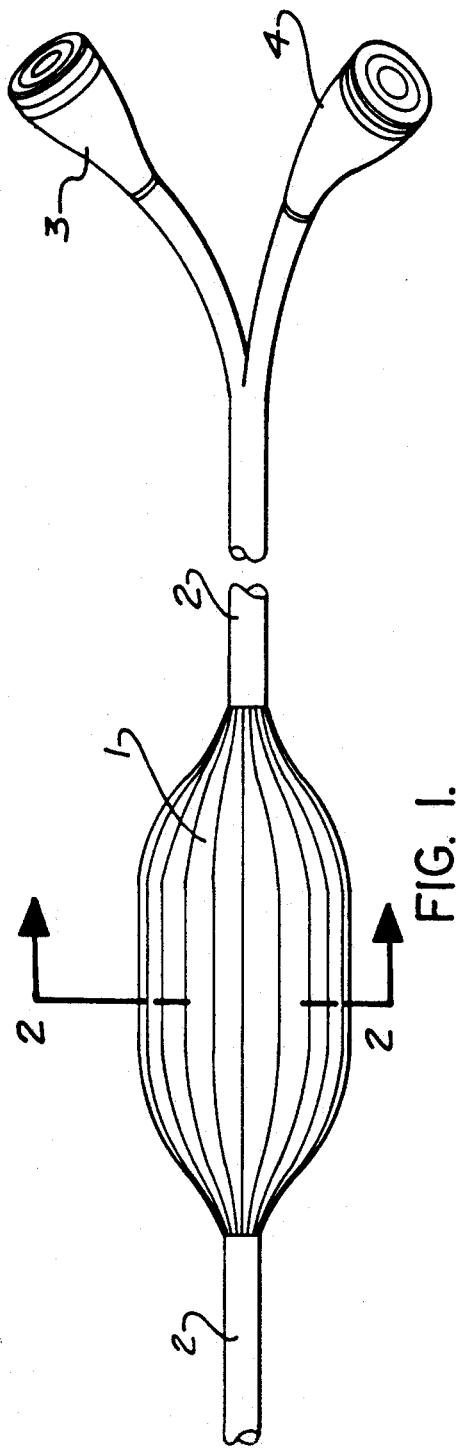
FIG. 1 is a side view of an arrangement including the balloon of the invention.

For the angioplasty dilatation treatment arrangements like the ones shown in FIG. 1 are used, comprising a catheter 2 having at least two lumens for passing the guiding cord or the contrast stuff and the other one to carry the liquid or air to inflate balloon 1.

The balloon 1 is mounted on catheter 2 at a predetermined distance from the point of entrance in the vessel to be treated.

At one end of catheter 2 there is a mouthpiece 3 for one of the lumens and another mouthpiece 4 for inflating balloon 1.

Figure 2:
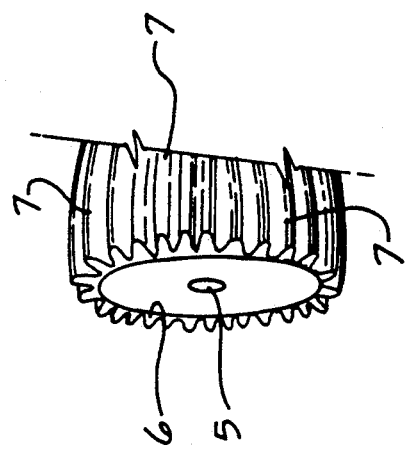
FIG. 2 is a perspective view of the cross section of the balloon pointed out in FIG. 1.

In the cross section shown in FIG. 2 it can be seen that balloon 1 has an inner wall 6 defining the inflatable chamber and inside and passing through it the part 5 of catheter 2.

In the embodiment shown in FIG. 1 the external wall of the balloon 1 has a plurality of ribs 7 emerging from wall 6 of the balloon.

In a preferred embodiment, the external wall is formed by an engraved sheet that is adhesively bonded to the exterior of the inner wall 6, thereby forming the ribs 7.

The outer surface of each one of the ribs 7 is what contacts the vessel endothelium when balloon 1 is inflated, with which, with the balloon inflated the surfaces in contact are only approximately 10% of the balloon external surface, hence substantially decreasing the damage produced by the balloon 1 in the endothelium.

FIGS. 3 and 4 show another preferred embodiment of the invention in which ribs 7 of the balloon are obtained by dividing the balloon into several balloons 8 placed in parallel and arranged radially around the part 5 of the catheter, each of the balloons having common inflating entrances from the part 5 of the catheter 2.

FIG. 5a shows a cross section of an artery before being treated by balloon angioplasty wherein it is shown the adventitia 10, the media 11 and the tissue of the intima 12, over which it is the endothelium 13.

If an angioplasty treatment is performed by means of a known conventional balloon, the pressure of the inflated balloon will flatten and destroy endothelium 13, as shown in FIG. 5b.

When using the balloon of present invention only a small part of endothelium 13 will suffer flattening and it will remain partially preserved as shown in FIG. 5c.

If a great number of endothelium cells are preserved anatomically and functionally intact, their presence will predominate in regard to antithrombogenicity and integrity protection of the surface preventing adhesion of platelets and blood cells.

Figure 6A:
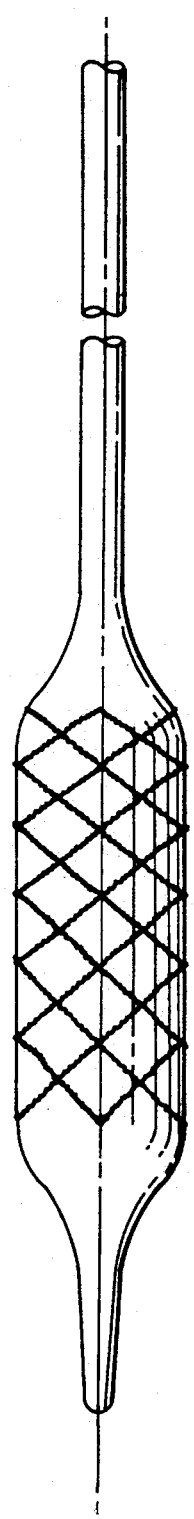
FIGS. 6a, 6b and 6c show alternative shapes of the surface of the balloon of the invention.
Figure 6B:
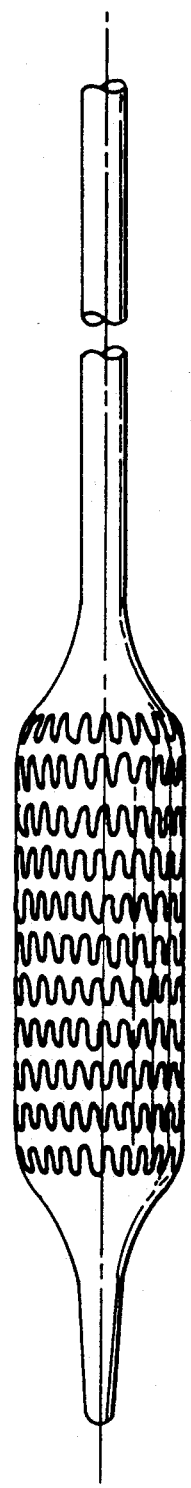
Figure 6C:
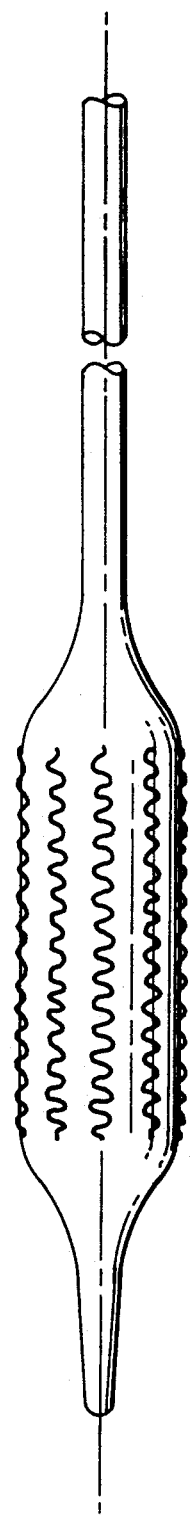

The external surface of the balloon, in order to diminish as much as possible its contact with the endothelium, may have several forms like the ones shown in FIGS. 6a, 6b and 6c.

Another characteristic of this type of ballons is that their surface is nonskidding, which admits the dilatation of fibrous injuries producing a smaller disection of the intima.

What we claim is:

1. A less traumatic angioplasty balloon for arterial dilatation of the type inflatable by means of respective lumens existing in a catheter used for the introduction of the balloon, the catheter and balloon defining a longitudinal axis, characterized in that the balloon has a unitary construction and the surface of the fully inflated balloon that contacts the endothelium of the vessel being treated is an irregular surface defining a plurality of elongate grooves and projecting parts interspersed therebetween.

2. An angioplasty balloon according to claim 1, wherein said irregular surface defines a plurality of longitudinal grooves.

3. An angioplasty balloon according to claim 1, wherein said irregular surface defines grooves that are disposed at an angle relative to the axis of the balloon, whereby the grooves intercross to form a net shape.

4. An angioplasty balloon according to claim 1, wherein said projecting parts of said irregular surface are defined by projections orderly placed along the surface.

5. An angioplasty balloon according to claim 1, wherein said irregular surface of the balloon is formed by the adhesion of an engraved sheet to the exterior of a wall of the balloon.

6. A less traumatic angioplasty balloon for arterial dilatation of the type inflatable by means of respective lumens existing in a catheter used for the introduction of the balloon, the catheter and balloon defining a longitudinal axis, characterized in that the surface of the fully inflated balloon that contacts the endothelium of the vessel being treated is an irregular surface defining a plurality of elongate grooves and projecting parts interspersed therebetween, wherein the grooved surface of the balloon is defined by the fact that the balloon is divided into a group of cylindrical balloons arranged in parallel with a common inflation entrance.

* * * * *

UNITED STATES PATENT AND TRADEMARK OFFICE
CERTIFICATE OF CORRECTION

PATENT NO. : 5,250,070
DATED : October 5, 1993
INVENTOR(S) : Juan C. Parodi

It is certified that error appears in the above-identified patent and that said Letters Patent is hereby corrected as shown below:

| COLUMN | LINE | |
|---|---|---|
| 1 | 9 | before the second paragraph insert --Background of the Invention-- |

Signed and Sealed this

Twenty-sixth Day of April, 1994

Attest:

BRUCE LEHMAN

*Attesting Officer*  *Commissioner of Patents and Trademarks*